US00RE38575E1

(19) United States
(12) Reissued Patent
Kohno et al.

(10) Patent Number: US RE38,575 E
(45) Date of Reissued Patent: Aug. 31, 2004

(54) DIAGNOSTIC METHOD FOR DIABETES USING C-13 LABELED PYRUVIC ACID

(75) Inventors: Tadashi Kohno, Tokyo (JP); Isaburo Hosoi, Tokyo (JP); Junko Hirayama, Tokyo (JP); Kunihiko Shibata, Tokyo (JP)

(73) Assignee: Tokyo Gas Company, Ltd., Tokyo (JP)

(21) Appl. No.: 10/147,001

(22) Filed: May 16, 2002

Related U.S. Patent Documents

Reissue of:
(64) Patent No.: 6,214,317
Issued: Apr. 10, 2001
Appl. No.: 09/294,616
Filed: Apr. 19, 1999

U.S. Applications:
(

(62) Division of application No. 08/918,378, filed on Aug. 26, 1997, now Pat. No. 5,916,538.

(30) Foreign Application Priority Data

Aug. 27, 1996 (JP) ..... 8-225243
Sep. 25, 1996 (JP) ..... 8-253040

(51) Int. Cl.[7] ..... A61K 49/00; G01N 33/497; A61B 5/08

(52) U.S. Cl. ..... 424/9.1; 436/900; 600/531; 600/532

(58) Field of Search ..... 424/9.1, 9.3, 1.81; 514/866; 436/900; 600/531, 532

(56) References Cited

PUBLICATIONS

Helge et al., In Baillie et al. EDS, Carbon–13 dioxide breathe tests in normal diabetic children following injestion of C–13 glucose, Stab. Isotop. Proc. Int. Symp., London, pp. 227–234, 1977.*

Cohen, S. Effects of Insulin on Perfused Liver from Streptozotocin–Diabetic and Untreated Rats, Biochemistry, 26(2), pp. 573–580, 1987.*

* cited by examiner

*Primary Examiner*—Michael G. Hartley
(74) *Attorney, Agent, or Firm*—Davidson, Davidson & Kappel, LLC

(57) ABSTRACT

The present invention relates to a diagnostic agent for diabetes, which comprises glucose labelled with $^{13}C$ at a specific position, or pyruvic acid labelled with $^{13}C$ at least one specific position. According to the present invention, there is provided a diagnostic agent for diabetes which can be used safely without side effects to give accurate results immediately with less physical pains on the subject. The present diagnostic agent for diabetes can distinguish between healthy persons and patients with diabetes even under the circumstances where the patients are easily missed, and further it can determine the type of diabetes (insulin-dependent type or insulin-independent type).

2 Claims, 12 Drawing Sheets

Main Metabolic Pathway of Glucose

Breath Sampling System from Rat

3-$^{13}$C-Glucose Breath Test vs Fructosamine Level in Blood

△ Normal
◪ Insulin-independent diabetes
● Insulin-dependent diabetes

DIAGNOSTIC METHOD FOR DIABETES USING C-13 LABELED PYRUVIC ACID

Matter enclosed in heavy brackets [ ] appears in the original patent but forms no part of this reissue specification; matter printed in italics indicates the additions made by reissue.

This application is a divisional of U.S. Ser. No. 08/918,378, filed Aug. 26, 1997, U.S. Pat. No. 5,916,538.

BACKGROUND OF THE INVENTION

1. Field of the Invention

The present invention relates to a diagnostic agent for diabetes and in particular to a diagnostic agent for diabetes which comprises glucose labelled with $^{13}C$ at a specific position, or pyruvic acid labelled with $^{13}C$ at least one specific position.

2. Description of the Prior Art

Test methods generally used in the primary screening in diagnosis of diabetes are urine sugar test and fasting blood sugar levels test. These tests are simple and high in specificity, but are low in sensitivity and give negative results for patients with light diabetes, so 70% or more patients are missed and these tests are considered inadequate as screening tests for diabetes (Sekikawa et al., Medical Practice 10:63, 1993). On the other hand, a glucose tolerance test used for the diagnosis of diabetes brings about side effects due to administration of a large amount of glucose, and this test requires the restraint of a subject for several hours and repeated collection of blood, and imposes heavy physical burdens on the subject, and further the procedures are troublesome, so this test is actually impossible to carry out as a screening test of diabetes. Recently, blood HbAlC and fructosamine tests, which reflect average of blood sugar levels for a certain period in the past, have been introduced as screening tests of diabetes in some facilities. Under the existing circumstances, however, even those tests are cannot be said to be adequate in sensitivity and specificity for light diabetes, and there remain the problem of a difference in measurement results among facilities.

Blood sugar level, HAlC and fructosamine tests have been used widely for diagnosis of the type of diabetes, management of outpatients with diabetes, and evaluation of therapeutic effects. However, blood sugar levels would drop at the time of fasting in the case of light diabetes, while besides the above-described problems, the HAlC and fructosamine tests have the problem that the results of the tests cannot be known until a next visit to the hospital, so instructions would be given to the patient on the basis of the past test results.

Under such circumstances, there is demand for developments in a test method which is effective for patients even with light diabetes and non-invasive to the subjects and which give results immediately and accurately for diagnosis of diabetes, management of patients with diabetes and evaluation of therapeutic effects.

On the one hand, it is generally carried out to administer $^{13}C$-labeled glucose and measure $^{13}C$ exhausting as carbon dioxide into an exhalation in order to assess energy expenditure. Because this analysis should be conducted under steady state, glucose should be administered for a long period before examination [J. J. Robert et al., J. Appl. Physiol. 63, 1725–1732 (1987)]. Therefore, this analysis requires a long period for examination and imposes the heavy pains on the subject, and is thus practically not usable for diagnosis of diabetes.

It is reported that after naturally labelled $^{13}C$-glucose prepared from $C_4$ plants is bolus administered, the degree of exhalation of $^{13}CO_2$ is reduced in the case of patients with diabetes [P. Lefebvre, et al., Diaetologia 14, 39–45 (1978); M. J. Arnaud, et al., Nutrition and the Diabetic Child, Pediat. Adolesc. Endocr. vol. 7, pp. 203–212, 1979]. However, because naturally labelled $^{13}C$-glucose have 6 carbons randomly labeled, we can scarcely evaluate an alternation of the metabolic pathway of glucose. Further, because the concentration of $^{13}C$ in naturally labelled $^{13}C$-glucose is 2% or thereabout, it is necessary to administer a large amount of glucose in order to monitor a change in the concentration of $CO_2$ in an exhalation, and the burdens on the subject are therefore heavy.

OBJECTS AND SUMMARY OF THE INVENTION

The object of the present invention is to provide a diagnostic agent for diabetes to give accurate results immediately with few pains on the subject.

As a result of their eager research, the present inventors found that diabetes and its type can be accurately diagnosed by administering glucose labelled with $^{13}C$ at a specific position or pyruvic acid labelled with $^{13}C$ at least one specific position, and then determining degrees of increase of $^{13}C$ levels in exhaled $CO_2$, and they thereby arrived at the completion of the present invention.

That is, the present invention relates to a diagnostic agent for diabetes comprising glucose labelled with $^{13}C$ at a specific position.

The present invention further relates to a diagnostic agent for diabetes comprising pyruvic acid labelled with $^{13}C$ at least one specific position.

DETAILED DESCRIPTION OF THE INVENTION

Figure 1:
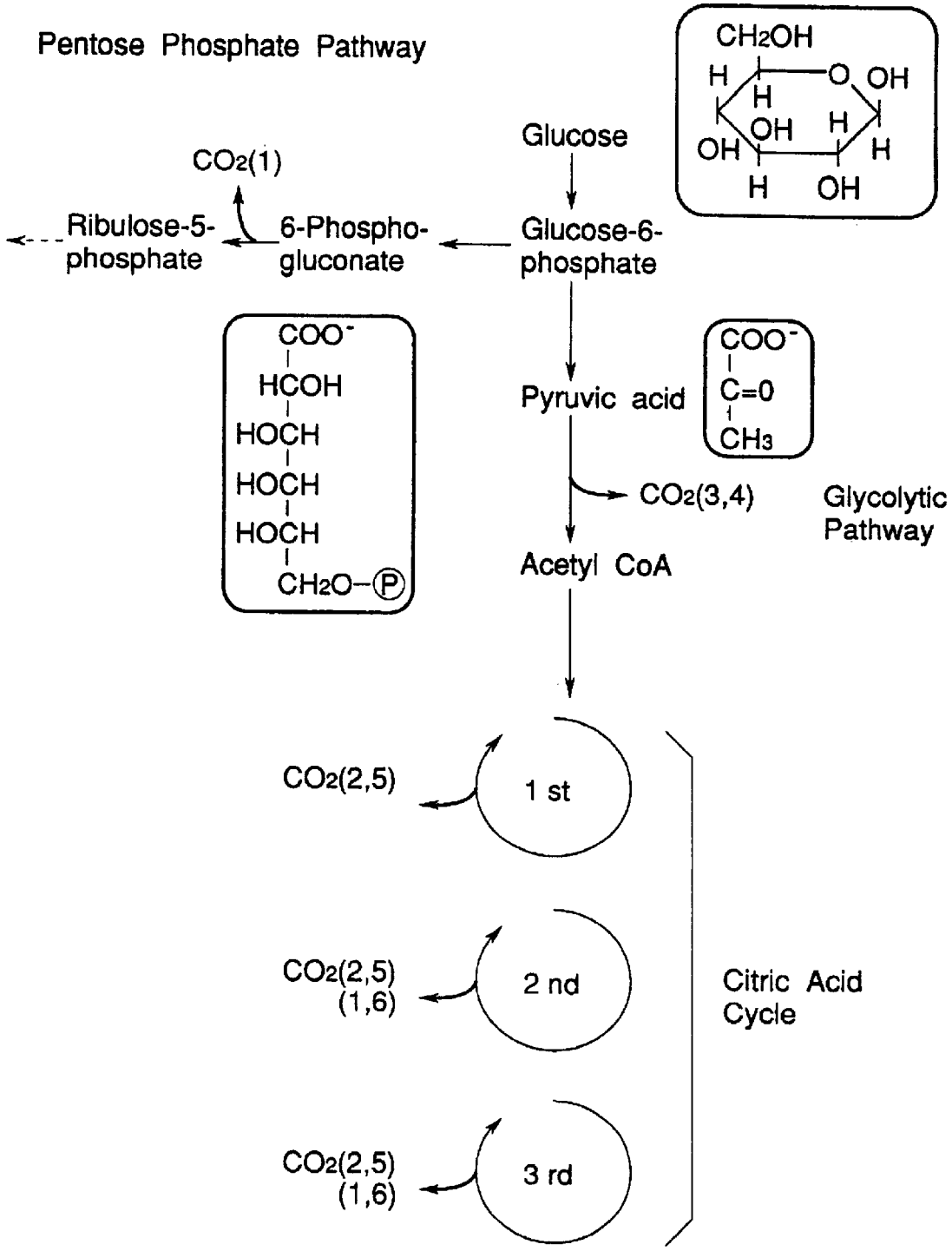
FIG. 1 shows the main metabolic pathway of glucose for decarboxylation (numbers in the brackets next to $CO_2$ indicate the position of carbon in glucose).

Hereinafter, the present invention is described in detail.

The glucose in the present diagnostic agent for diabetes is glucose labelled with $^{13}C$ at a specific position, and the labelled position may be any of positions 1 to 6.

Glucose labelled with $^{13}C$ at a specific position includes e.g. commercial products such as 1-$^{13}C$-glucose, 2-$^{13}C$-glucose, 6-$^{13}C$-glucose (produced respectively by EURISOTOP Ltd., CIL Ltd., ISOTEC Ltd. and ICON Ltd.), 3-$^{13}C$-glucose (produced by CIL Ltd. and ICON Ltd.), 4-$^{13}C$-glucose (produced by CIL Ltd.) and 5-$^{13}C$-glucose (produced by CIL Ltd.).

The pyruvic acid in the present diagnostic agent for diabetes is pyruvic acid labelled with $^{13}C$ at least one specific position.

The pyruvic acid in the present invention may be any pyruvic acid in which one, two or three of carbons at positions 1 to 3 have been labelled with $^{13}C$, preferably pyruvic acid labelled with $^{13}C$ at position 3. Specifically, commercial products such as sodium 3-$^{13}C$-pyruvate (produced by ICON Ltd.) etc. can be used.

Because $^{13}C$ is a stable isotope, there is no danger of exposure to radiation, and examinations can be effected safely.

In examinations using the present diagnostic agent for diabetes, $^{13}C$ levels ($\Delta^{13}C$ (%)) in exhaled $CO_2$ just after administration are determined followed by evaluation of data on degrees of increase of $^{13}C$ levels in exhaled $CO_2$ ($\Delta^{13}C$ (%)) at predetermined intervals (e.g. 5 minutes, 20 minutes) after administration, or on time course (slope at the start, change in the slope, peak time etc.) of degrees of increase of $^{13}C$ in exhaled $CO_2$ ($\Delta^{13}C$ (%)) for a predetermined time after administration. Although the sole evaluation by this breath test is useful, the result of this test is preferably combined with blood sugar levels, fructosamine levels etc. for synthetic judgment.

$^{13}C$ levels in exhaled $CO_2$ can be determined using gas chromatography mass spectrometry (GC-MS), infrared spectrophotometry, mass spectrometry, photoacoustic spectrophotometry and NMR (nuclear magnetic resonance).

The present diagnostic agent for diabetes can distinguish a group of diabetics from a normal group. In particular, the diagnostic agent for diabetes containing glucose labelled with $^{13}C$ can also distinguish the type of diabetes (whether diabetes is insulin dependent or independent).

Further, it is possible to obtain a material for evaluation, which depending on a difference in the position of carbon labelled with $^{13}C$ in glucose, is rendered special and advantageous to diagnosis of diabetes.

For example, glucose labelled with $^{13}C$ at position 1 (1-$^{13}C$-glucose) can distinguish between members with diabetes and healthy members in a group with normal fasting blood sugar levels, so this glucose is advantageous to the primary screening. Further, by virtue of its excellent relationship to the total amount of insulin secreted, this glucose is used advantageously to determine a course of action for therapy. Glucose labelled with $^{13}C$ at position 3 (3-$^{13}C$-glucose) can distinguish between patients with insulin-dependent diabetes and patients with insulin-independent type in the case of almost the same blood sugar levels, so this glucose is used advantageously for diagnosis of the type of diabetes. Moreover, this glucose may distinguish between the insulin-dependent diabetes and insulin-independent diabetes in the case of similar fructosamine levels, so it may be advantageously used for knowing an alternation in the disease (transition from the independent type to dependent type), which can be easily missed when evaluation is made using only fructosamine levels.

As shown in FIG. 1, carbons in glucose are decarboxylated in different metabolic pathways depending on their positions. Therefore, in cases where glucose labelled with $^{13}C$ at a specific position has been given, we can evaluate an alternation in the glucose metabolic pathways by determining the degree of exhalation of $CO_2$.

The present diagnostic agent for diabetes is manufactured into pharmaceutical preparations such as parenteral agents (tablets, capsules, powder, granules, liquid etc.), injections etc., depending on the administration route, by solely using glucose labelled with $^{13}C$ at a specific position (referred to hereinafter as labelled glucose) or pyruvic acid labelled with $^{13}C$ at least one specific position (referred to hereinafter as labelled pyruvic acid) or by mixing it with fillers or carriers. The fillers or carriers may be any of those conventionally used in this field if they are pharmaceutically acceptable. The type and composition of such preparations are altered suitably according to the route and method of administration. For example, water is used as a liquid carrier. As solid carriers, cellulose derivatives such as hydroxypropyl cellulose and organic acid salts such as magnesium stearate etc. are used. Water, physiological saline and various buffer solutions are generally desirable in the case of injections. Such preparations may be lyophilized for use as oral medicines, or the lyophilized preparations may be dissolved in suitable injection solvents e.g. liquids for intravenous administration, such as sterilized water, physiological saline, electrolyte etc. just before use.

The content of the labelled glucose or labelled pyruvic acid in the pharmaceutical preparation varies according to the type of pharmaceutical preparation, and is usually in the range of 10 to 100% by weight, preferably 50 to 100% by weight. In the case of injections, for example, the substituted glucose or substituted pyruvic acid is added usually in an amount of 1 to 40% by weight. In the next case of capsules, tablets, granules and powder, the content of the substituted glucose or substituted pyruvic acid is in the range of about 10 to 100% by weight, preferably 50 to 100% by weight, with the remainder being carriers.

The present diagnostic agent for diabetes should be administered at such a dosage as to enable confirmation of an increase of $^{13}C$ levels in an exhalation after administration. Depending on the age and weight of the patient and the object of breath test, the dosage for each administration ranges from about 1 to 2000 mg/kg body weight in the case of an adult.

Hereinafter, the present invention is described in more detail by reference to Examples, which however are not intended to limit the scope of the invention.

EFFECT OF THE INVENTION

According to the present invention, there is provided a diagnostic agent for diabetes which can be used safely without side effects and give accurate results immediately with less physical burdens on the subject. The present diagnostic agent for diabetes can not only distinguish between healthy persons and patients with diabetes even under the circumstances where the patients are easily missed, but can also determine the type of diabetes (insulin-dependent type or insulin-independent type).

PREFERRED EMBODIMENTS OF THE INVENTION

Test Example

[1] Materials and Methods (1) Animals

Male Sprague-Dawley strain (SD) rats were purchased from Nippon Charles River K.K. Neonatal rats were purchased along with a lactating rat. The rats were bred at 23° C.±2° C. under 55±10% humidity before use. The rats were fed standard diet and water ad libitum.

(2) Generation of diabetic rats

For insulin-dependent diabetes, insulin-deficient type diabetes was generated in a matured rat by intraperitoneally administering of streptozotocin (STZ) ("Saibokogaku" (Cell Engineering), Extra Issue, Medical Experiment Manual Series, Strategy for Study of Diabetes, edited by Susumu Kiyono and Yoshikazu Oka, published by Shushunsha, Japan).

STZ (No. S-0130, a product of Sigma) was administered intraperitoneally at a dose of 90 mg/kg to the matured rat previously fasted overnight. Two days later, blood was collected from the tail vein, and its blood sugar level was determined using Terumo Mediace (blood sugar measurement set), and a rat with at least 400 mg/dl was selected from rat thus treated. STZ was dissolved in a citrate buffer (pH 4.5) and administered within 5 minutes after it was dissolved.

For insulin-independent diabetes, insulin secretion-deficient type diabetes was generated by administering streptozotocin (STZ) to neonatal rats ("Saibokogaku", Extra Issue, Medical Experiment Manual Series, Strategy for Study of Diabetes, edited by Sussumu Kiyono and Yoshikazu Oka, published by Shushunsha, Japan).

STZ was subcutaneously administered at a dose of 90 mg/kg at 2 days old. At 4 days of age, blood was collected by cardiac puncture, and it blood sugar level was determined using Terumo Mediace (blood sugar measurement set), and a rat with at least 275 mg/dl was selected from rats thus treated. STZ was dissolved in a citrate buffer (pH 4.5) and administered within 5 minutes after it was dissolved.

(3) $^{13}$C breadth test

Figure 2:
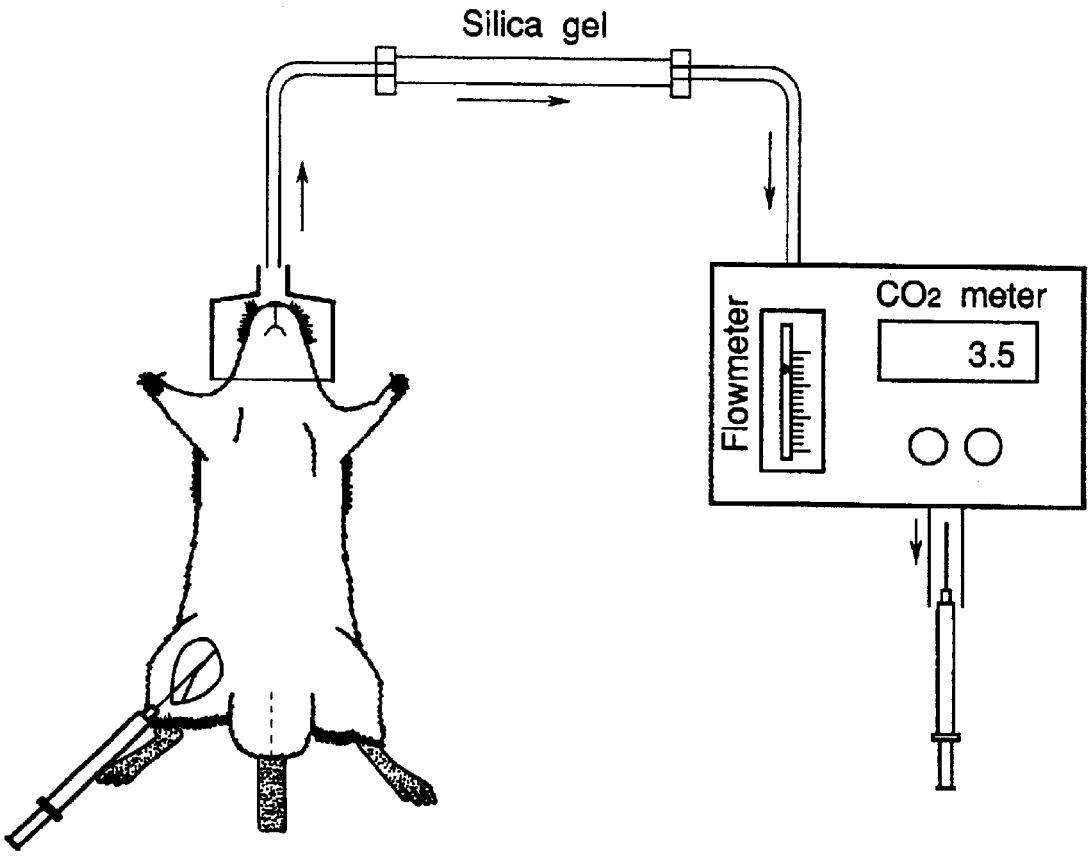
FIG. 2 shows a method of sampling an exhalation from a rat.

A rat fasted overnight was anesthetized by intraperitoneal administration of Nemutal (50 mg/kg) and fixed as shown in FIG. 2. Blood was collected from the tail vein, and its sugar level was determined using Terumo Mediace (blood sugar measurement set). 100 mg/kg $^{13}$C-glucose or sodium $^{13}$C-pyruvate (0.1 g/ml) dissolved in physiological saline was administered via the femoral vein, and the head was covered with a cylindrical tube, and its exhalation was sucked into a carbon dioxide meter CAPSTAR-100 (CWE, Inc.). An exhalation was collected in an volume of about 25 μl for each measurement through a Hamilton syringe (FIG. 2). The flow rate of the carbon dioxide meter was controlled such that its carbon dioxide level was within the range of 3.5±0.5%. The $^{13}$C level in exhaled $CO_2$ was determined in a gas chromatography mass spectrophotometer (GC-MS). The analytical conditions for GC-MS are as follows:

| [GC-MS conditions] | |
|---|---|
| Apparatus: | Shimadzu GC-MS QP-5000 [Shimadzu Co., Ltd.]. |
| Column: | 0.32 mm × 25 m (ID × L) fused silica capilliary column. |
| Ionization method: | EI (electron impact) method. |
| Gassification chamber temperature: | 60° C. |
| Column temperature: | 60° C. |
| GC interface temperature: | 230° C. |
| Carrier gas: | He. |
| Carrier gas pressure: | 20 Kpa. |
| Measurement mode: | SIM (selected ion monitoring). |
| Measurement ions: | m/z = 45, 46, 47. |

-continued

| [GC-MS conditions] | |
|---|---|
| Sample injection volume: | 20 μl. |

$^{13}$C-glucoses used were 1-$^{13}$C-glucose ($^{13}$C purity of carbon at the 1-position: 99 atom-%, a product of EURISOTOP Ltd. or CIL Ltd.), 2-$^{13}$C-glucose ($^{13}$C purity of carbon at the 2-position: 99 atom-%, a product of ISOTEC Ltd.), 3-$^{13}$C-glucose ($^{13}$C purity of carbon at the 3-position: 99 atom-%, a product of ICON Ltd.), and 6-$^{13}$C-glucose ($^{13}$C purity of carbon at the 6-position: 99 atom-%, a product of CIL Ltd. or ICON Ltd.). $^{13}$C-pyruvic acid used was sodium 3-$^{13}$C-pyruvate ($^{13}$C purity of carbon at the 3-position: 99 atom-%, a product of ICON Ltd.). The rectum temperature was monitored through the experiment, and the body temperature was kept at 37° C. on a warming mat. After the experiment was finished, whole blood was collected from the abdominal aorta and used as a sample for measurement of fructosamine level in blood. The analysis of fructosamine was entrusted to BML Ltd. After collection of blood, the rat used in the experiment was killed by administering an excess anesthetic.

Method of Calculating $^{13}$C levels

The ratio of the presence of an oxygen isotope in a sample was assumed to be the ratio in the nature, and its $^{13}$C level was calculated from the ion peak areas of m/z=45, 46 in the following formula. The ratio in areas of m/z=45, 46 (A45/A46) was assumed to be "a" according to Japanese Patent LOP Publication No. 120434/95.

$$^{13}\text{C level (\%)}=\{(0.004716-0.0007462a)\mathbf{2}/(0.9944396+0.00034298a)\}\times 100 \quad \text{(Formula 1)}$$

$\Delta^{13}$C (%) Calculation Method

Calculated from $^{13}$C level in exhaled $CO_2$($^{13}$C t min.) and $^{13}$C level in $CO_2$ standard gas ($^{13}$C std) at each point in the following formula:

$$\Delta^{13}\text{C level (\%)}=\{(^{13}\text{C t min.}-^{13}\text{C 0 min.})/^{13}\text{C std}\}\times 100 \quad \text{(Formula 2)}$$

(4) Measurement of insulin levels in blood

A by-path was formed by cannulation between the femoral artery and femoral vein in a rat previously fasted overnight under anesthesia by intraperitoneal administration of Nembutal (50 mg/kg). The by-path was provided with a branch through which heparin (No. 15077-019, a product of GIBCO. BRL) was administered (100 U/rat). After $^{13}$C-glucose (0.1 g/ml) dissolved in physiological saline was administered (100 mg/kg) through the branch, blood was collected with time and examined for blood sugar levels and insulin levels. The insulin levels were determined using an insulin measurement kit (a product of Morinaga Seikagaku Kenkyusho, Japan).

[2] Results (1) 1-$^{13}$C-glucose breath test ①

Figure 3:
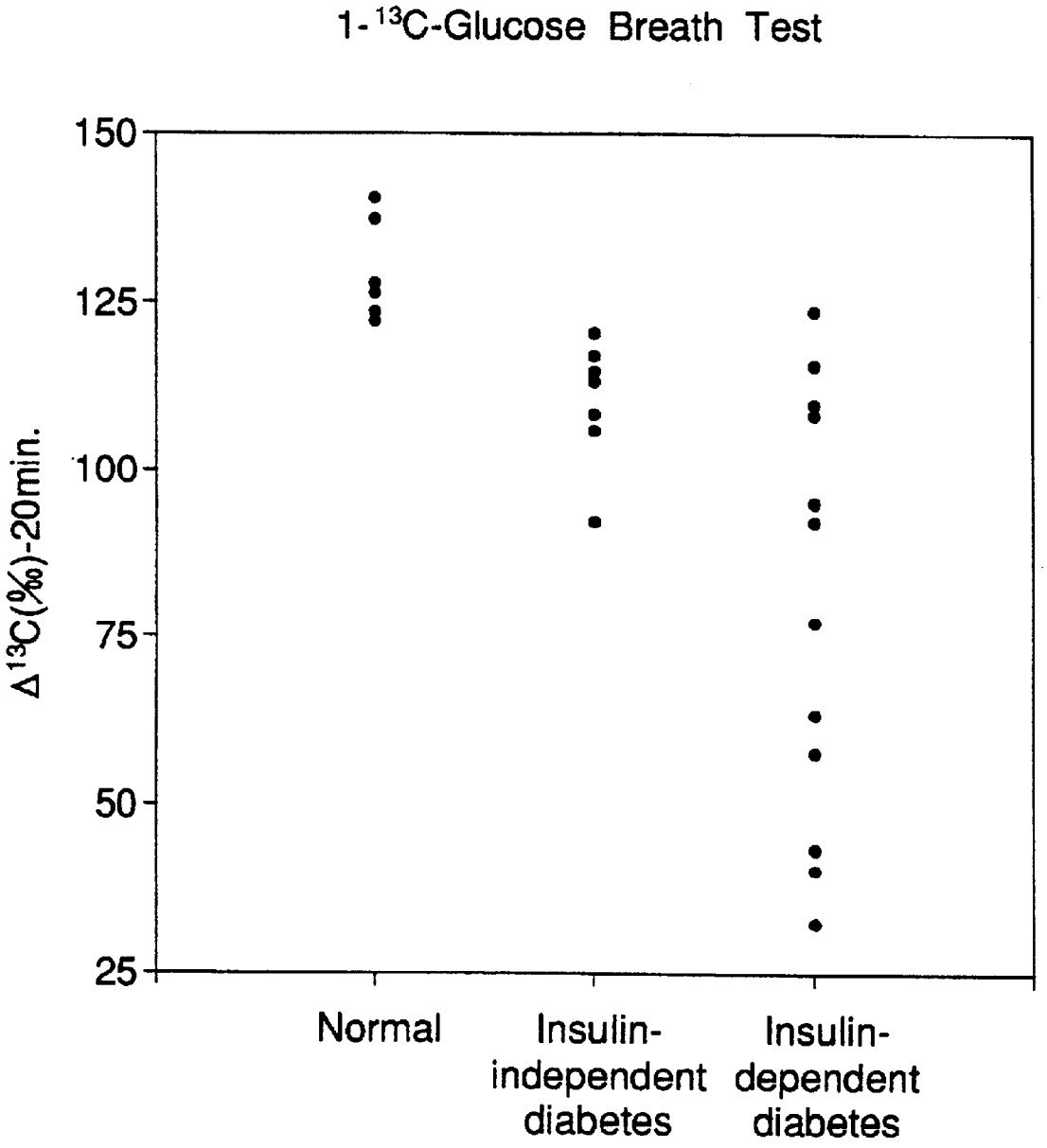
FIG. 3 shows degrees of increase of $^{13}C$ levels in exhaled $CO_2$ ($\Delta^{13}C$ (%)) twenty minutes after intravenous injection of 1-$^{3}C$-glucose (100 mg/kg).
Figure 4:
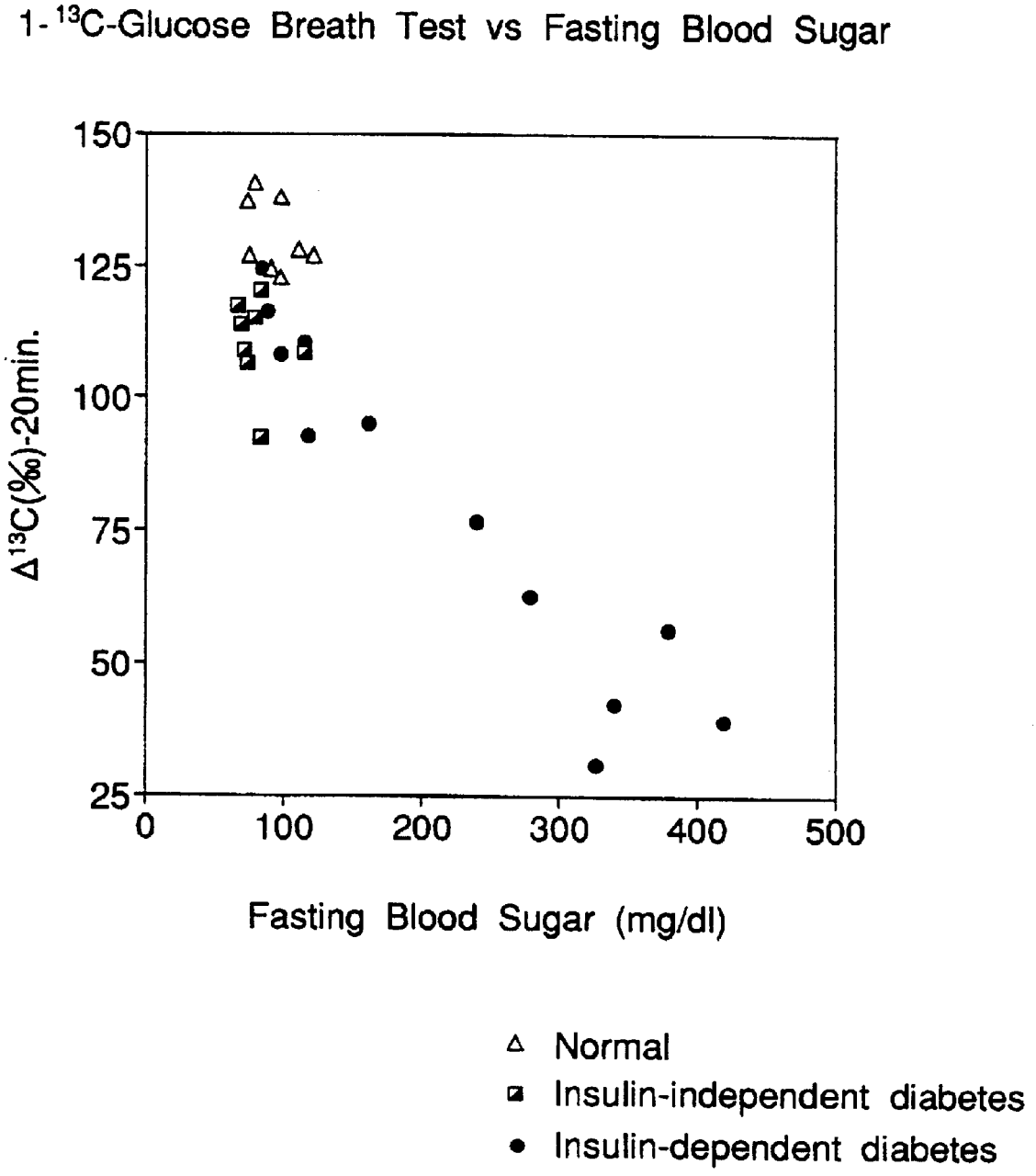
FIG. 4 shows the relationship between the 1-$^{13}C$-glucose breath test and fasting blood sugar levels.

Animals examined were male Sprague-Dawley strain (SD) normal rats (four 8-week-old rats and four 11-week-old rats), male SD rats with insulin-independent diabetes (four 8-week-old rats and four 11-week-old rat), and male SD rats with insulin-dependent diabetes (four 8-week-old rats, four 9-week-old rats, and four 11-week-old rats; STZ was administered when the rats were 7-week-old). FIG. 3 shows the results of the measurement of degrees of increase of $^{13}$C levels in exhaled $CO_2$ ($\Delta^{13}C$ (%)) at 20 minutes after intravenous injection of 100 mg/kg 1-$^{13}$C-glucose. FIG. 4 shows the results of the measurement of degrees of increase of $^{13}$C levels in exhaled $CO_2$ ($\Delta^{13}C$ (%)) at 20 minutes after intravenous injection of 100 mg/kg 1-$^{13}$C-glucose, versus blood sugar levels just before administration of the glucose.

The distribution of AC levels at 20 minutes after administration (FIG. 3) showed high levels over about 125 % in the normal rats while low levels below about 125 % in the rats with insulin-dependent diabetes and the rats with insulin-independent diabetes. It is assumed that in the case of higher sugar levels before administration, the degree of dilution of administered 1-$^{13}$C-glucose in blood is rendered higher, thus decreasing the degree of discharge of $^{13}$C into an exhalation. Actually, it is observed that $\Delta^{13}C$ levels decrease as blood sugar levels increases (FIG. 4). In the normal fasting blood sugar range (about 100 mg/dl), however, the $\Delta^{13}C$ levels in the animals with diabetes are lower than those of the normal animals even although both of them have almost the same fasting blood sugar levels (FIG. 4). Therefore, it can be said that the 1-$^{13}$C-glucose breath test does not only mean the degree of dilution of administered 1-$^{13}$C-glucose, that is, blood sugar levels.

As exemplified above, the 1-$^{13}$C-glucose breath test can distinguish between diabetes and normal in the same group with normal fasting blood sugar levels, and can thus serve as an accurate and superior primary screening method.

(2) 1-$^{13}$C-glucose breath test ②

Animals examined were male SD normal rats (five 11-week-old rats) and male SD rats with insulin-independent diabetes (five 11-week-old rats). The 1-$^{13}$C-glucose breath test and the measurement of insulin levels in blood were carried out in the same rats. 100 mg/kg of 1-$^{13}$C-glucose was administered into the rats through the branch of the by-path provided between the femoral artery and femoral vein. Blood was collected before administration and at 1, 2, 3, 5, 7, 10 and 15 minutes after administration, and insulin levels in blood were determined. FIG. 15 shows the total amount of insulin secreted for the 15 minutes after administration versus the determined increase of $^{13}$C levels in exhaled $CO_2$.

Figure 5:
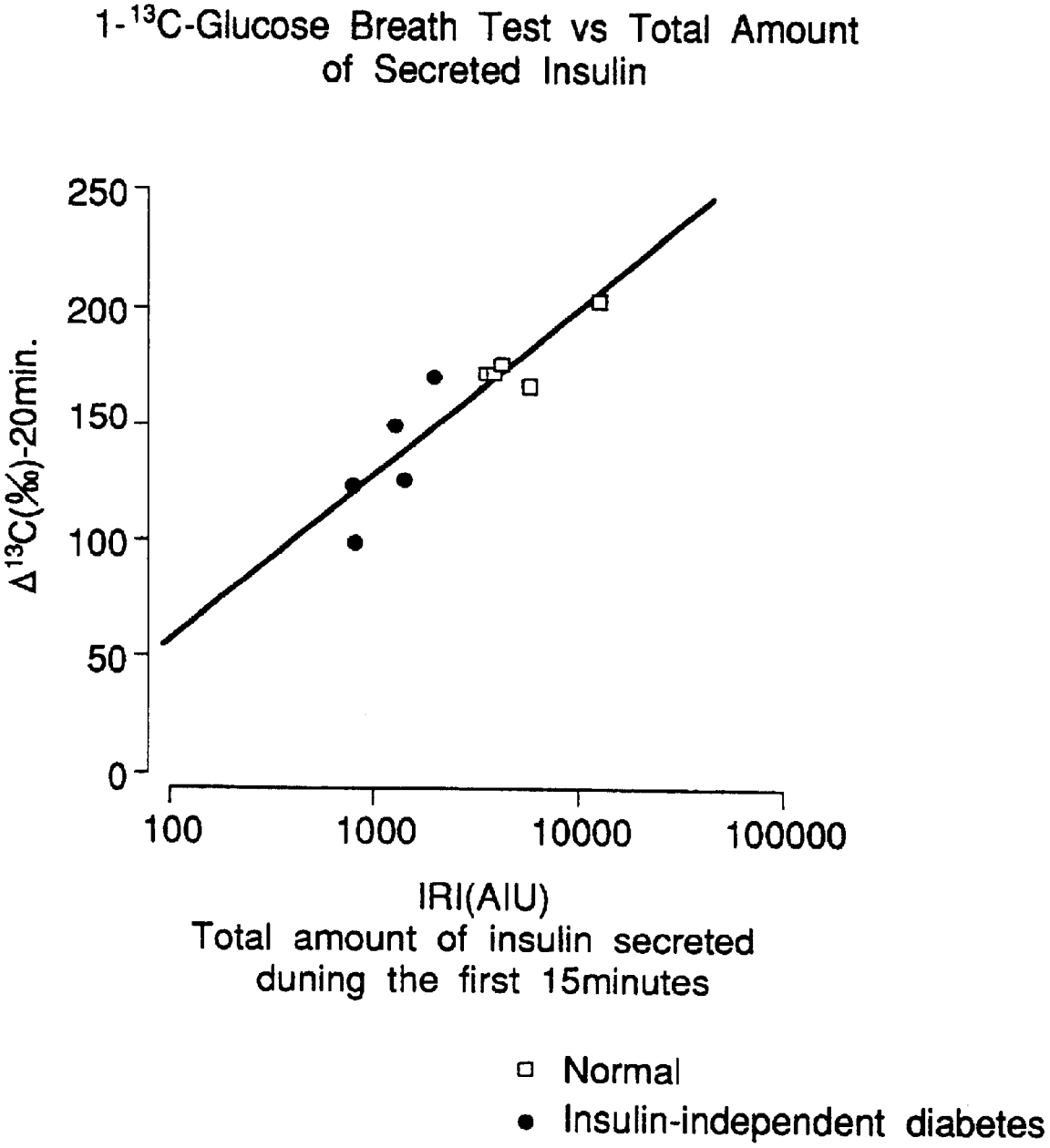
FIG. 5 shows the relationship between the 1-$^{13}C$-glucose breath test and the total amount of secreted insulin during the first 15 min.

Because the $\Delta^{13}C$ levels at 20 minutes after administration of the 1-$^{13}$C-glucose is in good relation with the total amount of insulin secreted for the first 15 minutes (FIG. 5), it is considered that this breath test is also useful as an examination method for determining a course of action for therapy.

(3) 3-$^{13}$C-glucose breath test ①

Figure 6:
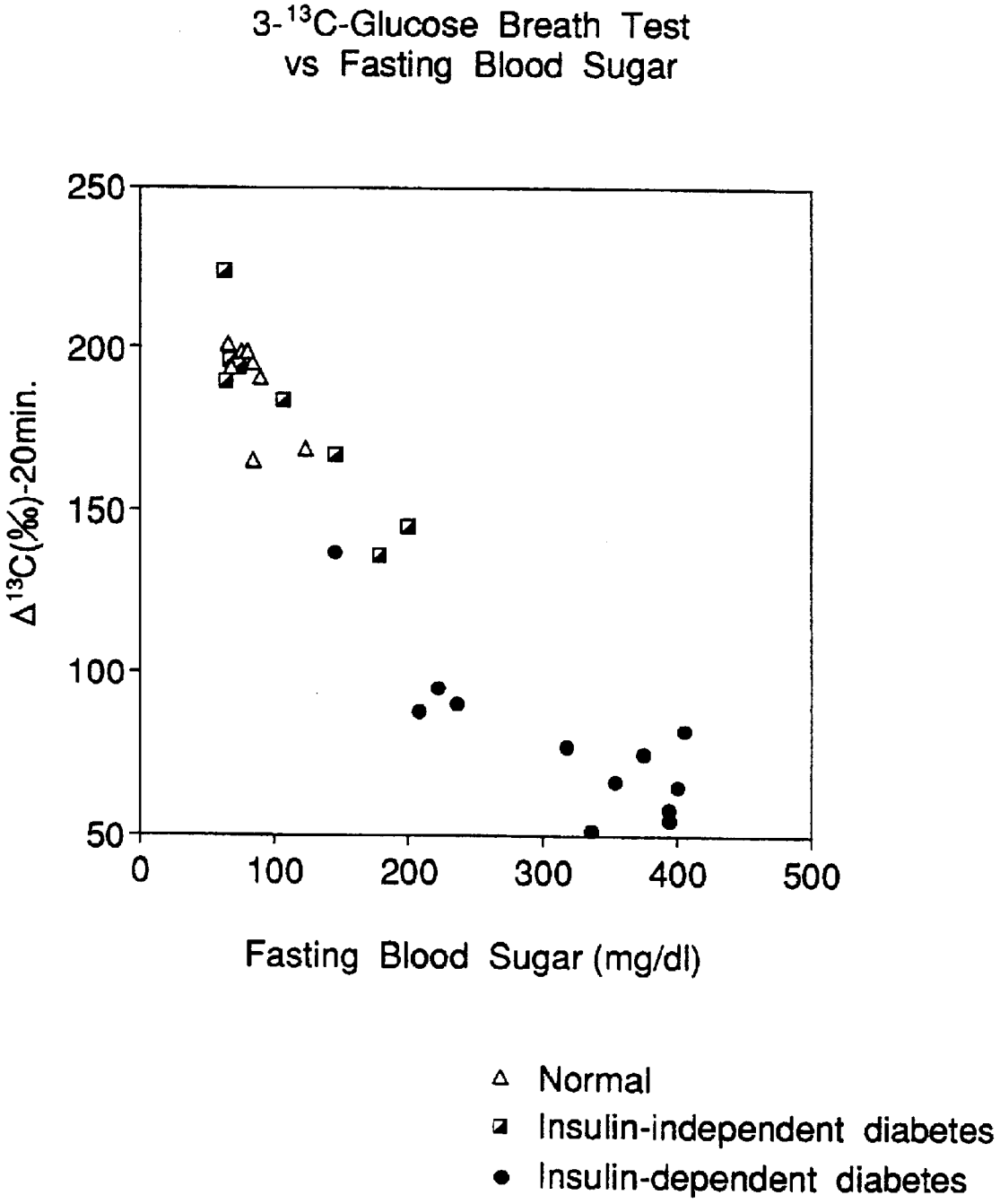
FIG. 6 shows the relationship between the 3-$^{13}C$-glucose breath test and fasting blood sugar levels.

Animals examined were male SD normal rats (four 8-week-old rats and four 11-week-old rats), male SD rats with insulin-independent diabetes (four 8-week-old rats and four 11-week-old rats), and male SD rats with insulin-dependent diabetes (four 8-week-old rats, four 9-week-old rats, and four 11-week-old rats; STZ was administered when the rats were 7-week-old). FIG. 6 shows the results of increase of $^{13}$C levels in exhaled $CO_2$ ($\Delta^{13}C$ (%)) at 20 minutes after intravenous injection of 100 mg/kg 3-$^{13}$C-glucose, versus fasting blood sugar levels before administration of the glucose.

The distribution of $\Delta^{13}C$ levels at 20 minutes after administration (FIG. 6) indicates that owing to the influence of blood sugar levels before administration, $\Delta^{13}C$ levels tend to decrease as blood sugar levels increase, as is the case with the 1-$^{13}$C-glucose breath test. However, insulin-dependent diabetes group tends to show lower $\Delta^{13}C$ levels compared with insulin-independent group, in spite of similar fasting blood sugar levels between both groups. Therefore, this breath test is considered usable for the diagnosis of the type of diabetes in combination with the measurement of fasting blood sugar levels.

(4) 3-$^{13}$C-glucose breath test ②

Animals examined were male SD normal rats (four 11-week-old rats), male SD rats with insulin-independent diabetes (six 11-week-old rats), and male SD rats with insulin-dependent diabetes (four 11-week-old rats; STZ was administered when the rat were 9-week-old).

Figure 7:
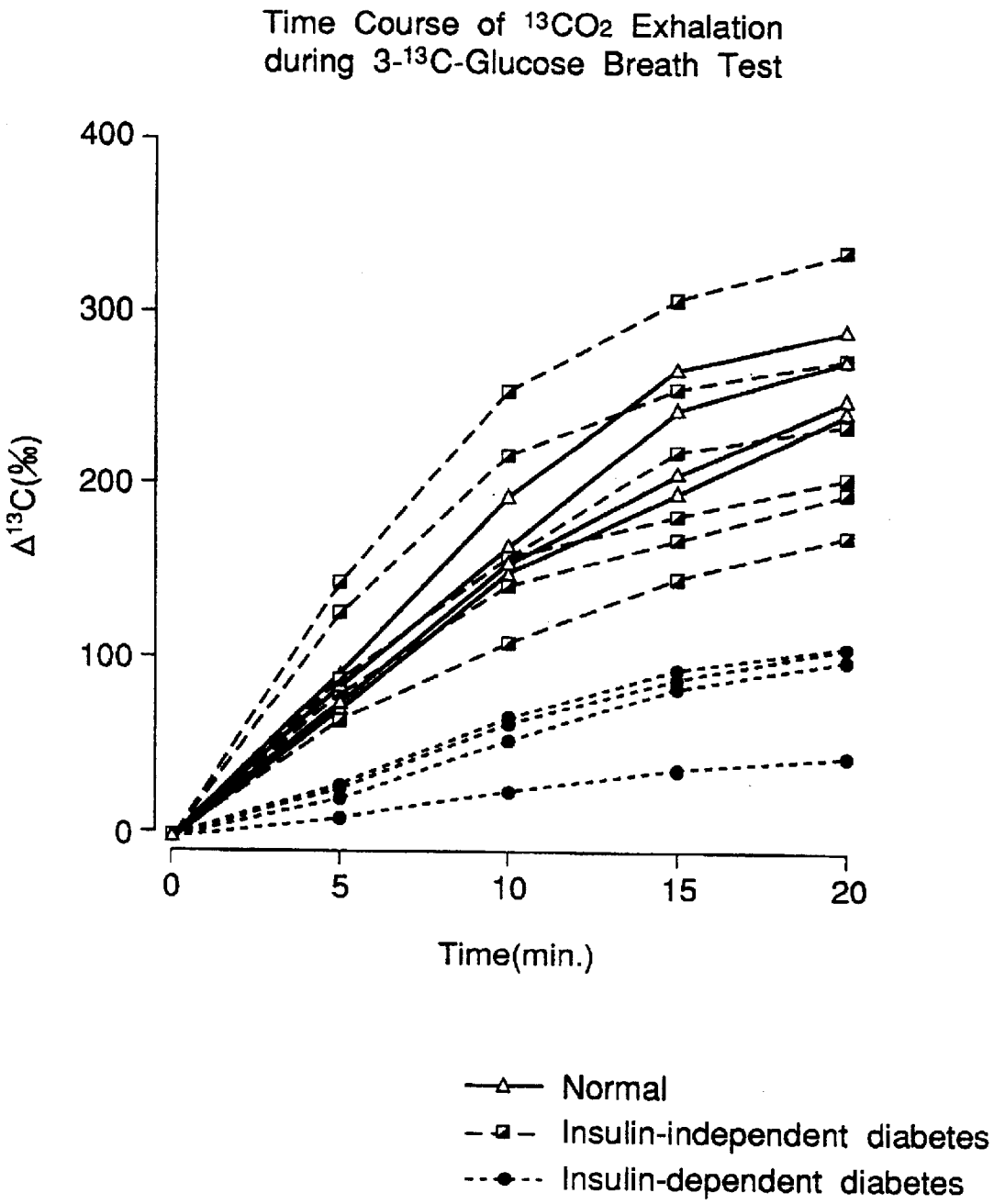
FIG. 7 shows the time course of $^{13}C$ levels in exhaled $CO_2$ ($\Delta^{13}C$ (%)) during the 3-$^{13}C$-glucose breath test.
Figure 8:
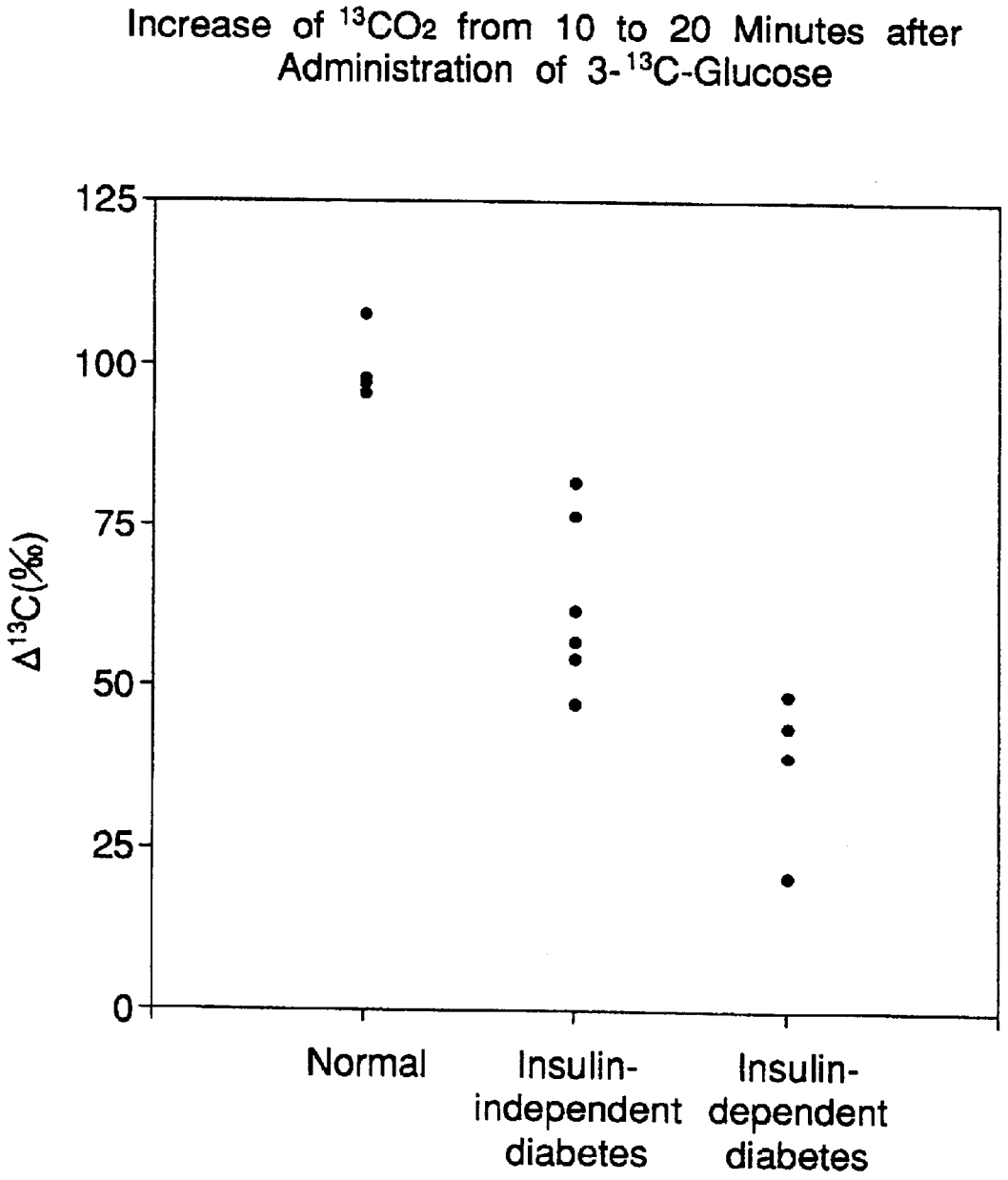
FIG. 8 shows degrees of increased of $^{13}C$ levels in exhaled $CO_2$($\Delta^{13}C$ (%)) from 10 to 20 minutes after administration of 3-$^{13}C$-glucose.

FIG. 7 shows the results of increase of $^{13}$C levels in exhaled $CO_2$ ($\Delta^{13}C$ (%)) at 5, 10, 15 and 20 minutes after intravenous injection of 100 mg/kg 3-$^{13}$C-glucose. In the curves of $\Delta C$ for the first 20 minutes after administration of 3-$^{13}$C-glucose (FIG. 7), the slope of the curve from the rats with insulin-independent diabetes tends to decrease in the later half. The curves at 10 to 20 minutes after administration indicate the following tendency of the slopes: normal rats>rats with insulin-independent diabetes>rats with insulin-dependent diabetes (FIG. 8). Therefore, 3-$^{13}$C-glucose breath test can be used for both diagnosis of diabetes and diagnosis of the type of diabetes.

(5) 3-$^{13}$C-glucose breath test ③

Figure 9:
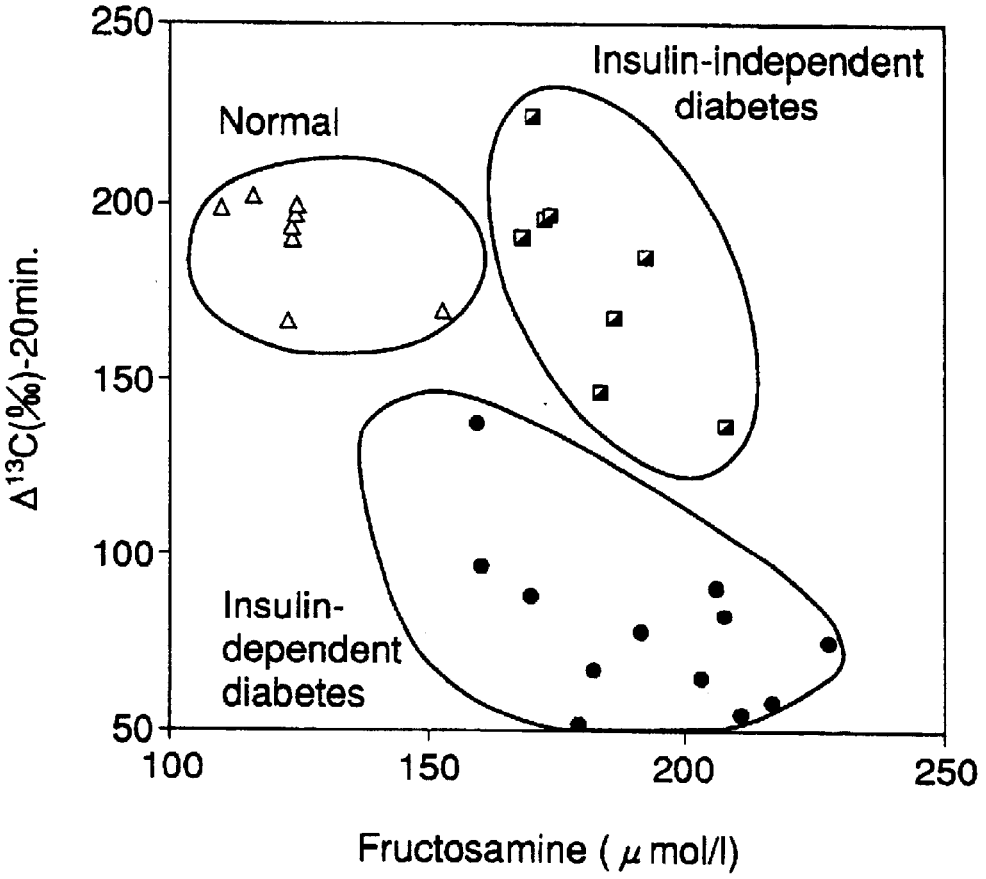
FIG. 9 shows the relationship between the 3-$^{13}C$-glucose breath test and fructosamine levels in blood.

Animals examined were male SD normal rats (four 8-week-old rats and four 11-week-old rats), male SD rats with insulin-independent diabetes (four 8-week-old rats and four 11-week-old rats), and male SD rats with insulin-dependent diabetes (four 8-week-old rats, four 9-week-old rats and four 11-week-old rats; STZ was administered when the rats were 7-week-old). FIG. 9 shows the results of increase of $^{13}$C levels in exhaled $CO_2$ ($\Delta^{13}C$ (%)) and fructosamine levels in blood at 20 minutes after intravenous administration of 100 mg/kg 3-$^{13}$C-glucose.

When $\Delta^{13}C$ levels and fructosamine levels at 20 minutes after administration are plotted, $\Delta^{13}C$ levels in the rats with insulin-dependent diabetes were lower than those in the rats with insulin-independent diabetes even though both of them have similar fructosamine levels (FIG. 9). Many reports have revealed that patients with symptoms of insulin-dependent diabetes at a first stage of the onset undergo transition to insulin-independent diabetes at a larger stage. Depending on such change in symptoms, it is necessary to alter methods such as insulin treatment etc., but conventional tests for determining only average blood sugar levels in terms of fructosamine, HbAIC etc. can miss such change. Accordingly, the 3-$^{13}$C-glucose breath test is also useful as a test for knowing such change in symptoms.

(6) 2-$^{13}$C-glucose and 6-$^{13}$C-glucose breath tests

Figure 10:
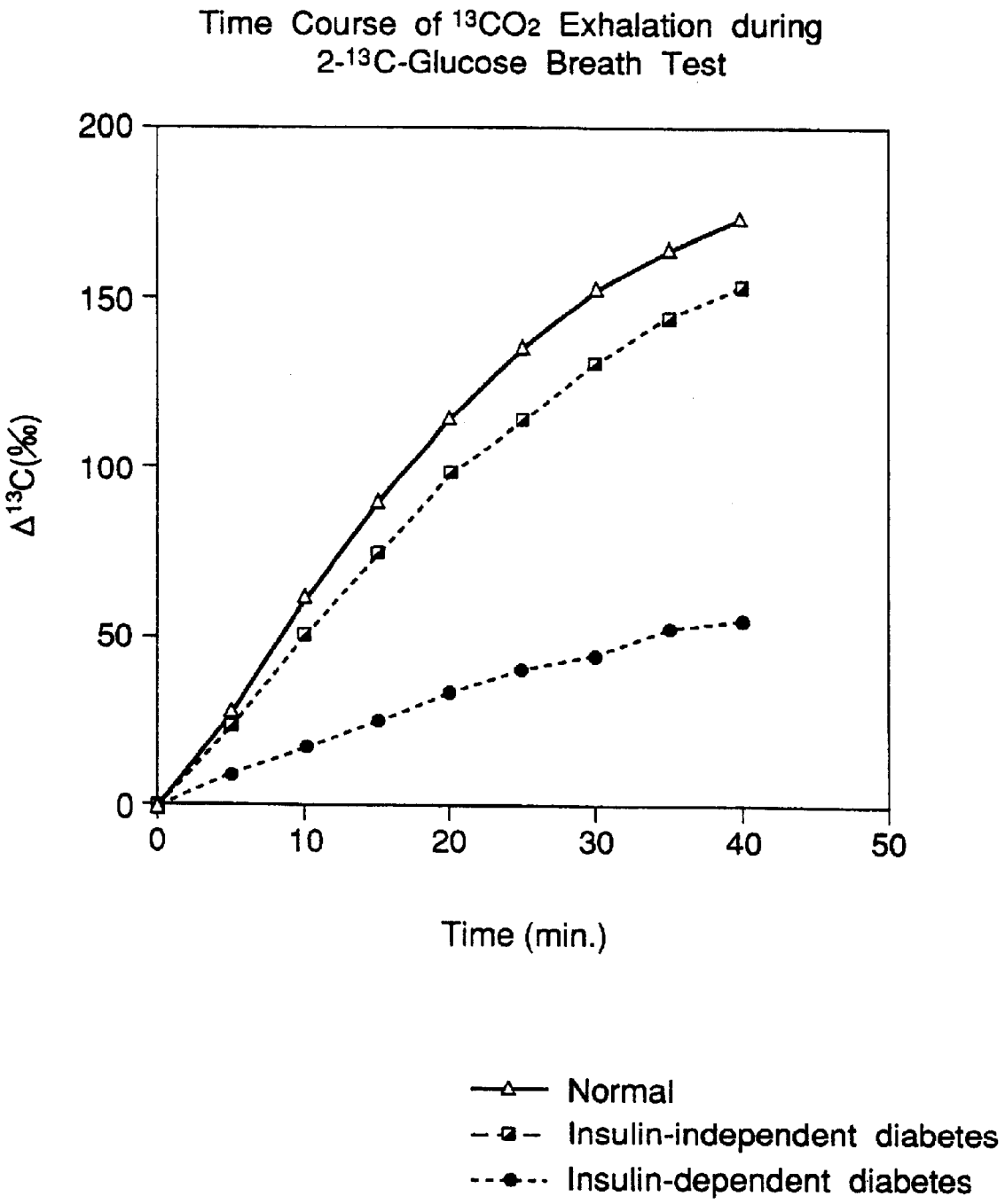
FIG. 10 shows the time course of $^{13}C$ levels in exhaled $CO_2$($\Delta^{13}C$ (%)) during the 2-$^{13}C$-glucose breath test.
Figure 11:
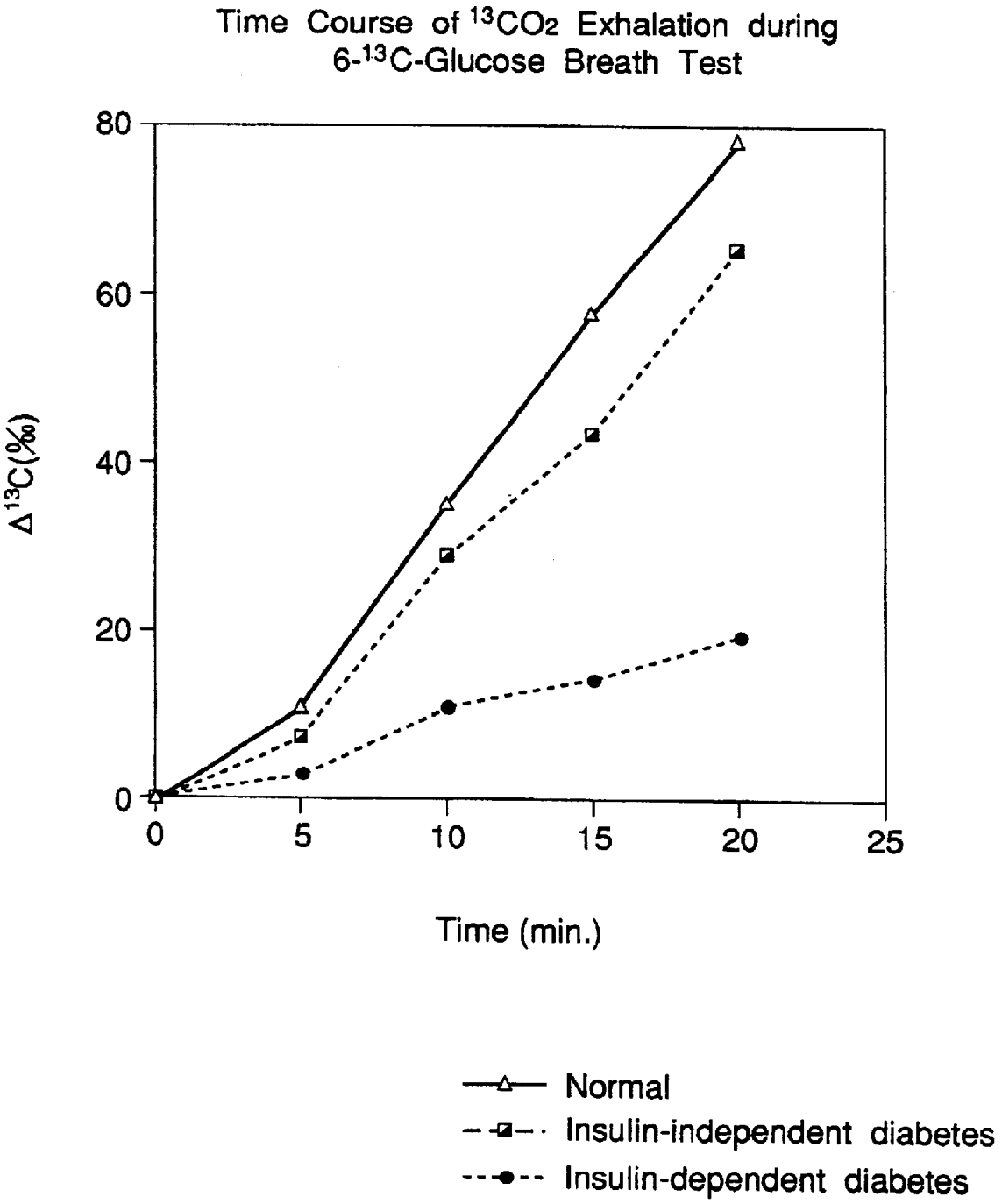
FIG. 11 shows the time course of $^{13}C$ levels in exhaled $CO_2$($\Delta^{\overline{\ }}C$ (%)) during the 6-$^{13}C$-glucose breath test.

Animals examined were male SD normal rats (two 8-week-old rats), male SD rats with insulin-independent diabetes (two 8-week-old rats), and male SD rats with insulin-dependent diabetes (two 8-week-old rats). FIG. 10 shows the time course of $^{13}$C levels in exhaled $CO_2$ ($\Delta^{13}C$ (%)) for 40 minutes after intravenous injection of 2-$^{13}$C-glucose. FIG. 11 shows the time course of $^{13}$C levels in exhaled $CO_2$ ($\Delta^{13}C$ (%)) for 20 minutes after intravenous injection of 6-$^{13}$C-glucose. Both of the 2-$^{13}$C-glucose breath test (FIG. 10) and 6-$^{13}$C-glucose breath test (FIG. 11) show that $\Delta^{13}C$ levels in the rats with insulin-dependent diabetes are lower than those in the rats with insulin-independent diabetes, so both of the breath tests can be considered usable in diagnosis of the type of diabetes.

(7) 3-$^{13}$C-pyruvate breath test

Figure 12:
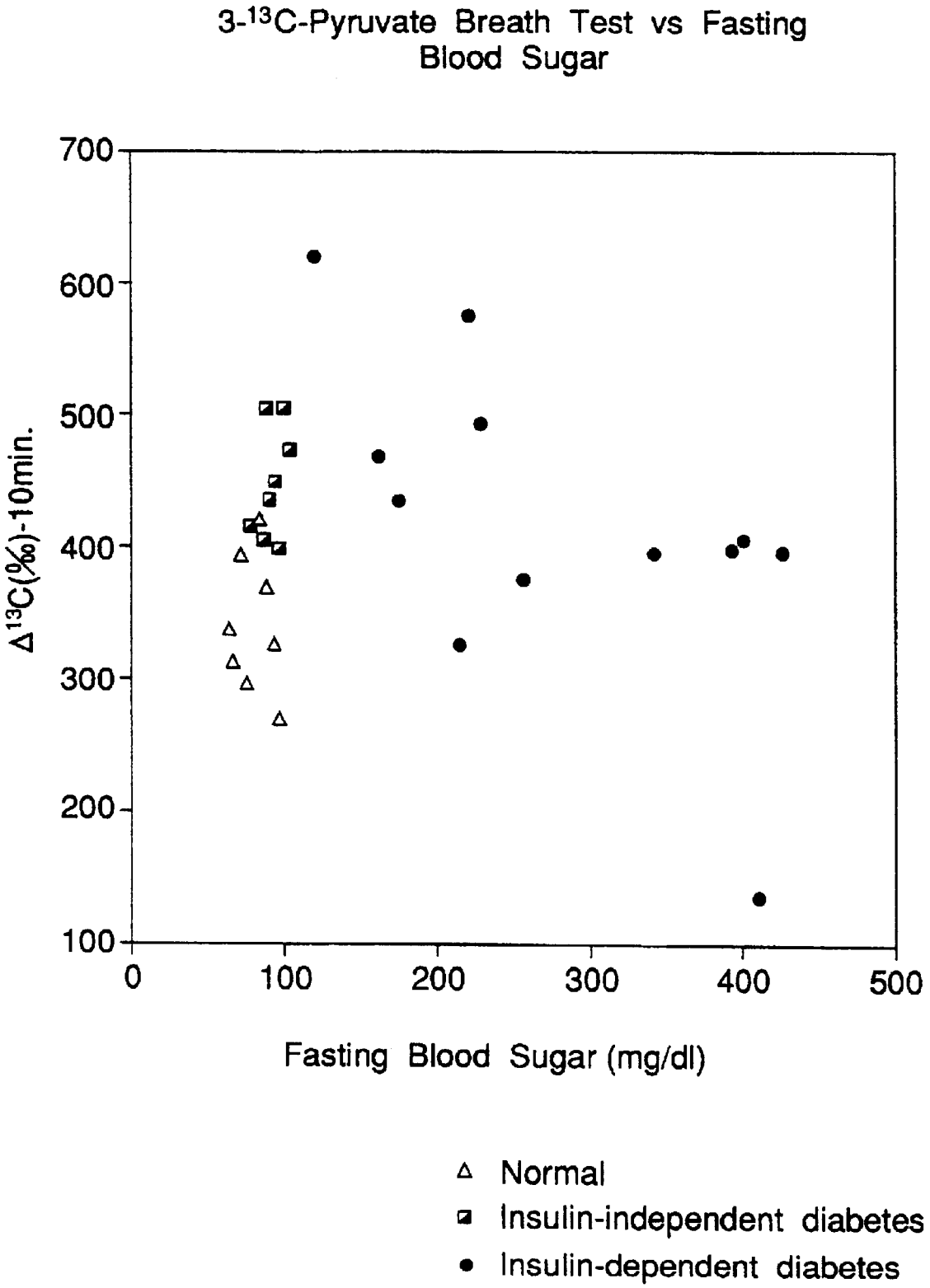
FIG. 12 shows the relationship between the 3-$^{13}C$-pyruvate breath test and fasting blood sugar levels.

Animals examined were male Sprague-Dawley strain (SD) normal rats (four 8-week-old rats and four 11-week-old rats), male SD rats with insulin-independent diabetes (four 8-week-old rat and four 11-week-old rats), and male SD rats with insulin-dependent-diabetes (four 8-week-old rats, four 9-week-old rat and four 11-week-old rats; STZ was administered when the rats were 7-week-old). FIG. 12 shows the results of an increase of $^{13}C$ levels in exhaled $CO_2$ ($\Delta^{13}C$ (%)) for 10 minutes after intravenous injection of 100 mg/kg sodium 3-$^{13}C$-pyruvate and fasting blood sugar levels in the same rats just before administration of the pyruvate.

$\Delta^{13}C$ levels in the rats with insulin-dependent diabetes that maintain high fasting blood sugar levels (blood sugar levels of not less than 20 mg/dl) are distributed in the wide range from 100 to 600 (%). In the normal fasting blood sugar range of about 100 mg/dl, however, the normal rats show lower levels than about 40 (%) while the rats with insulin-independent diabetes and the rats with insulin-dependent diabetes with fasting blood sugar levels of not more than 200 mg/dl show higher levels than about 400 (%).

The fasting blood sugar test used for the primary screening in diagnosis of diabetes is considered to miss about ⅔ of patients with diabetes because their blood sugar levels are in the normal range. However, the present 3-$^{13}C$-pyruvate exhalation test can distinguish between members with diabetes and normal members in the same group having normal fasting blood sugar levels, and can thus serve as an accurate and superior primary screening method.

Pharmaceutical Preparation Example 1 (Injection)

10 parts by weight of 1-$^{13}C$-glucose was dissolved in 90 parts by weight of physiological saline and sterilized by filtration through a Millipore filter. The filtrate was introduced into a vial and sealed to give an injection.

Pharmaceutical Preparation Example 2 (Internal Liquid Agent)

10 parts by weight of 1-$^{13}C$-glucose was dissolved in 90 parts by weight of de-ionized water and sterilized by filtration through a Millipore filter. The filtrate was introduced into a vial and sealed to give an internal liquid agent.

Pharmaceutical Preparation Example 3 (Injection)

10 parts by weight of sodium 3-$^{13}C$-pyruvate was dissolved in 90 parts by weight of physiological saline and sterilized by filtration through a Millipore filter. The filtrate was introduced into a vial and sealed to give an injection.

Pharmaceutical Preparation Example 4 (Internal Liquid Agent)

10 parts by weight of sodium 3-$^{13}C$-pyruvate was dissolved in 90 parts by weight of de-ionized water and sterilized by filtration through a Millipore filter. The filtrate was introduced into a vial and sealed to give an internal liquid agent.

What is claimed is:

1. A method for detecting a diabetic condition in a subject comprising:

a) administering to said subject an effective amount of pyruvic acid labeled with $^{13}C$ at a specific position; and b) measuring a level of exhaled labeled $CO_2$, wherein [a reduced] *an increased* level of exhaled labeled $CO_2$ compared to normal is indicative of an increased likelihood of said subject having or suffering from said diabetic condition.

2. The method according to claim 1, wherein said pyruvic acid labeled with $^{13}C$ at a specific position is selected from the group consisting of 1-$^{13}C$-pyruvic acid, 2-$^{13}C$-pyruvic acid and 3-$^{13}C$-pyruvic acid.

* * * * *